(12) United States Patent
Habibi-Naini

(10) Patent No.: US 8,833,577 B2
(45) Date of Patent: Sep. 16, 2014

(54) CHILDPROOF CLOSURE FOR A DISPENSING APPARATUS

(75) Inventor: Sasan Habibi-Naini, Rikon (CH)

(73) Assignee: Sulzer Mixpac AG, Haag (CH)

( * ) Notice: Subject to any disclaimer, the term of this patent is extended or adjusted under 35 U.S.C. 154(b) by 130 days.

(21) Appl. No.: 13/218,309

(22) Filed: Aug. 25, 2011

(65) Prior Publication Data

US 2012/0061343 A1   Mar. 15, 2012

(30) Foreign Application Priority Data

Sep. 10, 2010 (EP) .................................... 10176212

(51) Int. Cl.
*B65D 50/00* (2006.01)
*B65D 50/04* (2006.01)
*B65D 81/32* (2006.01)
B65D 6/00 (2006.01)
A61C 5/06 (2006.01)
B05C 17/005 (2006.01)
B65D 35/30 (2006.01)

(52) U.S. Cl.
CPC ............... *B65D 50/041* (2013.01); *B65D 7/00* (2013.01); *B65D 2215/02* (2013.01); *A61C 5/064* (2013.01); *B05C 17/00509* (2013.01); *B65D 81/325* (2013.01); *B05C 17/00553* (2013.01); *B65D 50/00* (2013.01); *B65D 35/30* (2013.01)
USPC .......... 215/200; 215/222; 215/218; 215/201; 215/216; 215/277; 222/216; 222/137; 222/145.1; 222/145.6

(58) Field of Classification Search
CPC .......... B65D 50/00; B65D 55/02; B65D 7/00; B65D 35/30; B65D 50/046; B65D 50/041; E05B 73/0041; A61C 5/064; A61C 5/04
USPC ............... 215/222, 218, 217, 216, 277, 201; 222/103, 386, 387, 390, 277, 137, 145, 222/41, 153.09, 145.6, 145.1, 145.5, 333, 222/327; 206/807
See application file for complete search history.

(56) References Cited

U.S. PATENT DOCUMENTS 3,101,856 A * 8/1963 Whiteman, Jr. ................ 215/209
3,261,490 A * 7/1966 McDonald et al. ........... 215/221

(Continued)

FOREIGN PATENT DOCUMENTS

| EP | 1 125 641 A1 | 8/2001 |
|---|---|---|
| FR | 2 916 741 A1 | 12/2008 |
| GB | 1 441 341 A | 6/1976 |

*Primary Examiner* — Mickey Yu
*Assistant Examiner* — Gideon Weinerth
(74) *Attorney, Agent, or Firm* — Kilpatrick Townsend & Stockton LLP

(57) ABSTRACT

A childproof closure for a dispensing apparatus (5) having first bayonet fastening means (20), wherein the closure (40, 50, 80, 100) has second bayonet fastening means (21). One of the two bayonet fastening means (20, 21) has bayonet lugs (30, 32) which can be introduced into corresponding socket elements (25, 27) of the other bayonet fastening means (20, 21). Both bayonet fastening means (20, 21) moreover have coding elements (13, 23, 35, 38) for a preset alignment of the closure (40, 50, 80, 100) and of the dispensing apparatus (5). The closure (40, 50, 80, 100) has a closure element (40, 50) having first engagement elements (43, 70) and a securing cap (80, 100) which at least partly covers the closure element (40, 50) and has second engagement elements (75, 130). The securing cap (80, 100) and the closure element (40, 50) are connected cohesively strongly, but rotatably with respect to one another, by means of shape-matched elements (58, 60, 90, 120). The securing cap (80, 100) is configured at least partly elastically deformably such that the first and second engagement elements (43, 70, 75, 130) can be brought into engagement with one another by pressing the securing cap (80, 100) toward the closure element (40, 50).

14 Claims, 6 Drawing Sheets

(56) References Cited

U.S. PATENT DOCUMENTS

| | | | |
|---|---|---|---|
| 3,690,495 A * | 9/1972 | Turner | 215/220 |
| 3,734,331 A * | 5/1973 | De Felice | 215/217 |
| 3,782,600 A * | 1/1974 | Columbus | 222/94 |
| 3,797,688 A * | 3/1974 | Porcelli et al. | 215/220 |
| 4,410,098 A * | 10/1983 | Dubs et al. | 215/220 |
| 4,433,789 A * | 2/1984 | Gibilisco | 215/220 |
| 4,979,942 A * | 12/1990 | Wolf et al. | 604/83 |
| 5,033,650 A * | 7/1991 | Colin et al. | 222/137 |
| 5,038,963 A * | 8/1991 | Pettengill et al. | 222/145.3 |
| 5,092,477 A * | 3/1992 | Johnson et al. | 215/230 |
| 5,137,182 A * | 8/1992 | Keller | 222/153.1 |
| 5,197,616 A * | 3/1993 | Buono | 215/220 |
| 5,280,842 A * | 1/1994 | Koo | 215/220 |
| 5,401,169 A * | 3/1995 | Fleisher et al. | 433/90 |
| 5,638,970 A * | 6/1997 | Garby et al. | 215/219 |
| 5,769,252 A * | 6/1998 | Volpe | 215/221 |
| 6,024,256 A * | 2/2000 | Beck et al. | 222/153.06 |
| 6,053,343 A * | 4/2000 | Krueger | 215/209 |
| 6,286,722 B1 * | 9/2001 | Fischer et al. | 222/137 |
| 6,394,314 B1 * | 5/2002 | Sawhney et al. | 222/137 |
| 6,843,652 B2 * | 1/2005 | Xie et al. | 433/90 |
| 6,854,613 B2 * | 2/2005 | Biesecker et al. | 215/219 |
| 7,111,746 B2 * | 9/2006 | Miceli et al. | 215/219 |
| D607,326 S * | 1/2010 | Branson et al. | D9/453 |
| 7,694,853 B2 * | 4/2010 | Keller | 222/137 |
| 8,074,843 B2 * | 12/2011 | Keller | 222/137 |
| 8,209,944 B1 * | 7/2012 | Miceli et al. | 53/490 |
| 8,235,616 B2 * | 8/2012 | Raccah | 401/129 |
| 8,316,622 B2 * | 11/2012 | Jajoo et al. | 53/329 |
| 8,333,288 B2 * | 12/2012 | Miller et al. | 215/216 |
| 8,590,719 B2 * | 11/2013 | Sprishen et al. | 215/216 |
| 2003/0197024 A1 * | 10/2003 | Sawhney et al. | 222/137 |
| 2008/0257849 A1 * | 10/2008 | Farrar et al. | 215/222 |
| 2009/0230214 A1 * | 9/2009 | Keller | 239/338 |
| 2010/0163579 A1 * | 7/2010 | Keller | 222/137 |
| 2011/0094990 A1 * | 4/2011 | Sprishen et al. | 215/217 |
| 2011/0095026 A1 * | 4/2011 | Habibi-Naini | 220/315 |
| 2012/0097708 A1 * | 4/2012 | Obrist et al. | 222/137 |
| 2012/0228329 A1 * | 9/2012 | Staub | 222/137 |
| 2013/0105515 A1 * | 5/2013 | Frey et al. | 222/137 |
| 2014/0117044 A1 * | 5/2014 | Pappalardo | 222/137 |

* cited by examiner

CHILDPROOF CLOSURE FOR A DISPENSING APPARATUS

CROSS REFERENCE TO RELATED APPLICATIONS

This application claims the priority of European Application No. 10 176 212.8, filed on Sep. 10, 2010, the disclosure of which is incorporated herein by reference.

FIELD OF THE INVENTION

The invention relates to a childproof closure for a dispensing apparatus having bayonet fastening with a childproof closure to prevent children from unauthorized access to substances in the dispensing apparatus.

BACKGROUND OF THE INVENTION

Dispensing apparatus and in particular multicartridges for mixing and discharging multicomponent materials are known from EP-A-0730913, for example. A closure cap or a mixer element is fastened to the dispensing apparatus by means of a bayonet closure.

In many cases, substances are used in such dispensing apparatus which are chemically more or less aggressive and whose ingestion or contact with the skin has to be prevented since otherwise poisoning or chemical burns of persons or animals can occur. Whereas adults are generally in control of the correct handling of such substances, there is in particular the risk with children that they consider the content of the dispensing apparatus for something edible and ingest it.

BRIEF SUMMARY OF THE INVENTION

It is the object of the present invention to propose a childproof closure for a dispensing apparatus having bayonet fastening means which in particular prevents children from unauthorized access to such substances present in the dispensing apparatus.

This object is satisfied by a dispensing apparatus having the features disclosed herein. Advantageous aspects and expedient further developments of the invention are set forth in the dependent claims.

The closure in accordance with the invention requires the coordination of different movement procedures with an additional application of force for the opening of the dispensing apparatus, which cannot be effected by children, in particular small children. As a consequence, the proposed closure is childproof.

The childproof closure is in particular suitable for a multi component cartridge containing a plurality of cylindrical containers. The childproof closure is preferably suitable for a double-cartridge for dispensing two components. The containers preferably contain cylindrical chambers. The chambers, i.e. the inner space of the hollow-cylindrical cartridge containers, can have a cylindrical shape or an elliptical or polygonal cross-section. The multi component cartridge also includes an expulsion plunger which has a shape-matched piston for each chamber.

The multicomponent cartridges also include, in addition to the cylindrical chambers, a molding serving as an outlet part. In this respect, the outlet part relates, for example, to a totality of tubular moldings of the individual chambers and/or a cylindrical connector part. The outlet part can be engaged over by the closure and has an output opening for every component at the closure side, i.e. the individual components are held separate from one another up to the end of the outlet part at the closure side so that a premature mixing of the components is prevented.

The outlet part of the multicomponent cartridge, for example, contains first bayonet fastening means. The closure thus contains corresponding second bayonet fastening parts. One of the two fastening means has bayonet lugs which can be introduced into corresponding socket elements of the other bayonet fastening means. Both bayonet fastening means expediently also have coding elements for a preset alignment of the closure and of the dispensing apparatus or multicomponent cartridge.

The childproof closure in accordance with the invention now has a closure element having first engagement elements and a securing hap having second engagement elements and at least partly covering the closure element. In addition, the securing cap and the closure element contain shape-matched elements which allow the cohesively strong connection of the closure element and of the securing cap such that the closure element and the securing cap remain freely rotatably supported with respect to one another as long as the securing element remains pressure-free with respect to the closure element, i.e. as long as no mechanical pressure is exerted onto the securing cap from the outside. The securing cap is configured at least partly elastically deformably such that the first and second engagement elements can be brought into engagement with one another by pressing the securing the cap against the closure element.

The securing cap preferably represents a beaker-like or cap-like element which is configured such that it can be pushed over the closure element. In this respect, the closure element and the securing cap are preferably hollow cylindrical elements having a base or cover, wherein the securing cap has a larger cross-section than the closure element so that the securing cap can be pushed with its hollow cylindrical part over the hollow cylindrical part of the closure element.

The closure element is preferably a beaker-like element having a hollow cylindrical part and a base, wherein the closure element has first engagement elements at its jacket surface, i.e. at the outer side of the hollow cylindrical part or at the outer side of the base.

The securing cap is preferably an element which can be pushed over the closure element and is likewise of beaker shape or of hat shape and has a hollow cylindrical part and a base, wherein the securing cap preferably has second engagement elements at its inner side, i.e. at the inner side of the hollow cylindrical part on the inner side of the base.

The securing cap is dimensioned such that the securing cap pushed over the closure element is freely rotatable with respect to the closure element in the mechanically non-strained state, i.e. the first and second engagement means are not in engagement with one another. In this respect, the expression "in the mechanically non-strained state" means that no external force is exerted onto the securing cap pushed over the closure element such as could occur, for example, by compressing the cap or by pushing or pressing the securing cap onto the closure element.

The engagement elements at the closure element as well as also at the securing cap are preferably made up of a saw tooth structure, i.e. ribs having the shape of saw teeth. The engagement elements of the closure element and of the securing cap nevertheless together preferably describe a saw tooth coupling.

The securing cap should be fixable captively, but freely rotatably in the pressureless state, at the closure element. This is preferably done by use of tongue and groove connection elements. For this purpose, the closure element, for example, has a groove which extends transversely to its concentric longitudinal axis and is peripheral or sector-shaped and the securing cap, for example, has a spring element which can engage elastically into the groove of the closure element and is molded to the securing cap. On the other hand, the securing cap can also have a groove which extends transversely to its concentric longitudinal axis and is peripheral or sector-shaped, wherein then the closure element has at least one spring element which can engage elastically into the groove and is molded to the closure element.

The socket elements of the dispensing apparatus or of the closure element, for example, represent ring-shaped or sector-shaped elements optionally having an undercut. The ring-shaped or sector-shaped elements thus serve for the at least partial shape-matched reception of the bayonet lugs.

The cut-outs at the socket elements, i.e. the free space located between two segment-shaped socket elements, as well as correspondingly designed bayonet lugs of different widths together preferably serve as coding elements. The latter are configured such that the bayonet lugs of the closure element or of the dispensing apparatus can only be introduced in a specific position with respect to the cut-outs of the ring-shaped or sector-shaped socket elements.

The socket elements and the dispensing apparatus are preferably configured in one piece, expediently in the form of a cast molded body. The bayonet lugs are likewise preferably molded in one piece to the closure element in the form of a cast molded body. Alternatively, the socket elements can also be configured in one piece with the closure element in the form of a cast molded body and the bayonet lugs can be molded to the dispensing apparatus in one piece as a cast body element.

Very preferably, the closure element represents a cylindrical element which has a saw tooth structure extending parallel to its concentric longitudinal axis at at least a part of its jacket surface, wherein the securing cap is configured as a beaker-like element having a hollow cylindrical part and a base and the inner side of the beaker-like element has a saw tooth structure which extends parallel to its concentric longitudinal axis and can engage into the saw tooth structure of the closure element. In this respect, the closure element has radially projecting segment-like bayonet lugs at the margin of its jacket surface directed toward the dispensing apparatus transversely to its concentric longitudinal axis.

In a further preferred embodiment, the closure element is a beaker-like element having a hollow cylindrical part and a base which has a radially outwardly extending saw tooth structure at at least a part of its outer base surface and the securing cap likewise represents a beaker-like element having a hollow cylindrical part and a base, wherein the inner side of the base of the securing cap has a saw tooth structure which extends radially outwardly and can engage into the saw tooth structure of the closure element. In this respect, the closure element again has radially projecting segment-like bayonet lugs at the margin of its jacket surface directed toward the dispensing apparatus transversely to its concentric longitudinal axis.

Further preferably, abutment flanks are present as a rotational boundary of the two bayonet fastening means at the dispensing apparatus or at the closure element and extend parallel to the longitudinal axis of the closure element and are arranged over the bayonet lugs.

The closure in accordance with the invention can represent a cap for closing a dispensing apparatus, but can also have a mixer element, in particular a static mixer element, which can be brought into fluid communication with the content of the dispensing apparatus, wherein the mixer element pierces the closure element and the securing cap, wherein further the closure element and the securing cap are configured as freely rotatable, but sealing, with respect to the mixer.

BRIEF DESCRIPTION OF THE DRAWINGS

The invention will be further explained below by way of example by the following Figures.

DETAILED DESCRIPTION OF THE INVENTION

Figure 1:
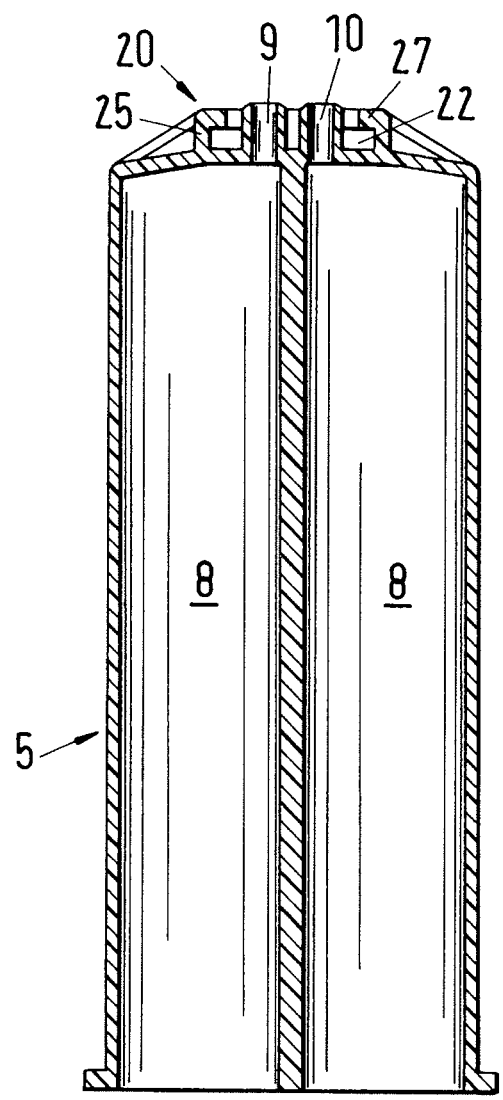
FIG. 1 is a longitudinal section of a double cartridge.

FIG. 1 shows a longitudinal section through a dispensing apparatus 5 which is configured as a double cartridge and which has two cylindrical containers of the same cross-sectional area for a metering ratio 1:1. The containers 8 open into two separate cylindrical and mutually spaced apart outlets 9 and 10. If a static two-component mixer is connected to the dispensing apparatus, the outlets 9, 10 of the dispensing apparatus fit into or onto the inlets of the mixer such that a tight connection results. The dispensing apparatus 5 furthermore has first bayonet fastening means 20 in the form of socket elements 25, 27. The socket elements describe a ring-shaped or segment shaped groove 22 extending around the outlets 9, 10 for receiving second bayonet fastening means.

Figure 2:
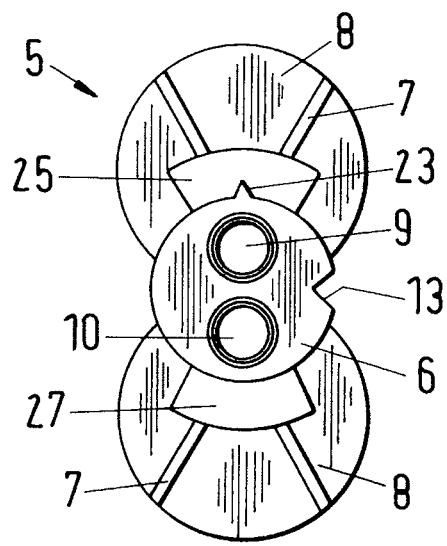
FIG. 2 is a plan view of the cartridge of FIG. 1.

FIG. 2 shows a plan view of the dispensing apparatus 5 shown in FIG. 1 having two cylindrical containers 8 of the same cross-section. The front side 6 of the dispensing apparatus 5 has, beside the outlets 9, 10, two mutually oppositely disposed segment-like socket elements 25 and 27, wherein the segment 25 is somewhat wider than the segment 27. The segment-shaped socket elements 25, 27 have correspondingly segment-shaped grooves 22 (see FIG. 1) which serve for the reception of bayonet lugs 30, 32 of the closure element 50 (see FIG. 3 and FIG. 4). The socket elements 25, 27 are reinforced by reinforcement ribs 7. The front side 6 of the dispensing apparatus 5 moreover has a V-shaped notch 13 as a visual coding means. The segment-shaped socket element 25 contains a radially inwardly open V-shaped recess 23 which can cooperate with a code nose 35 molded to the closure element (see FIG. 3) so that the closure element 50 can only be inserted in one direction, which is in particular of importance on a closure with an integrated mixer. The dispensing apparatus 5 configured as a double cartridge and having the two containers 8, the outlets 9 and 10, the segment-shaped socket elements 25 and 27 as well as the reinforcement ribs 7 together preferably form a cast plastic part, in particular an injection die cast part.

Figure 3:
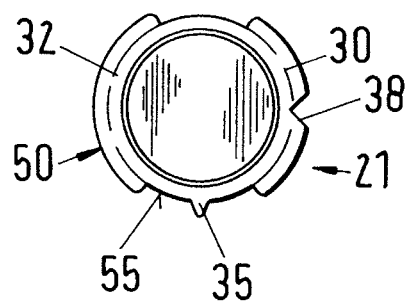
FIG. 3 is a plan view of the second bayonet fastening means of the closure element.

FIG. 3 shows a plan view of the second bayonet fastening means of a closure element 50 as well as of the cylindrical part 55 of the closure element 50. The closure element 50 has two segment-shaped bayonet lugs 30 and 32. The bayonet lug 30 moreover contains an outwardly open V-shaped notch 38 as a coding means which corresponds, for example, to the notch 13 of the dispensing apparatus 5 so that, with a closure element pushed, but not latched, into the socket elements of the dispensing apparatus 5, the notches 13 and 38 lie over one another, for example. The closure element 50 contains at its cylindrical part 55 a molded coding nose 35 which corresponds to the V-shaped recess 23 of the socket element 25 for introducing the closure into the bayonet socket 25, 27 of the dispensing apparatus 5. The notch 13 of the dispensing apparatus 5 can further correspond to the coding nose 35 with a closure element 50 completely latched into the socket elements of the dispensing apparatus 5, i.e. the coding nose 35 and the notch 13 then lie over one another. The bayonet lug 30, 32 and the coding nose 35 are preferably molded in one piece with the beaker-like closure element 50 so that the closure element, including bayonet lugs and coding nose, preferably represents a molded part, in particular a plastic injection molded part.

Figure 4:
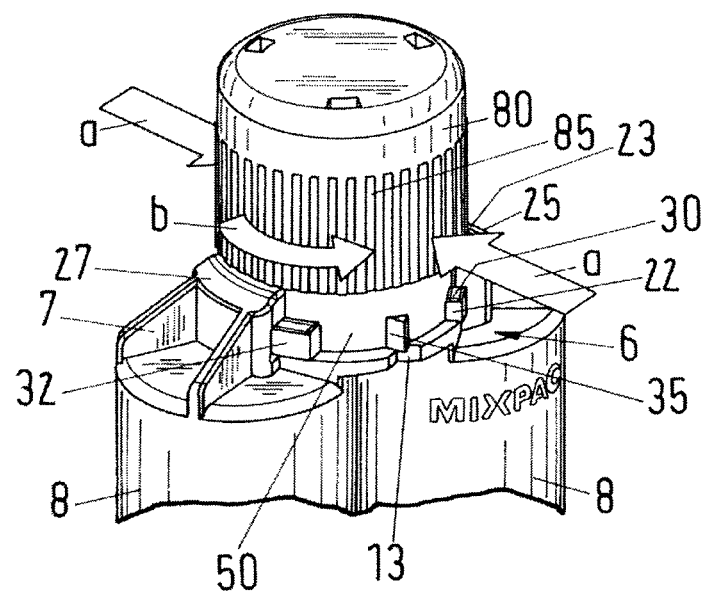
FIG. 4 is a perspective view of a first embodiment of a closure fastened onto a double cartridge by means of a bayonet closure.

FIG. 4 shows a perspective view of a first embodiment of a closure fastened onto a double cartridge by means of a bayonet closure. The double cartridge contains two containers 8 and segment-like socket elements 25, 27 are molded on the front side 6 of the cartridge and are stabilized in the radial direction by reinforcement ribs. The closure element 50 is fastened by means of bayonet lugs 30, 32 introduced into the segment-shaped groove 22 of the socket elements 25, 27. The bayonet lugs 30, 32 are molded in one piece to the closure element 50. The closure element 50 moreover has a coding nose 35 which in the closed state shown, i.e. with the bayonet lugs 30, 32 of the closure element 50 completely pushed into the socket elements of the cartridge, is aligned with the V-shaped notch 13 on the front side 6 of the cartridge. The closure element is mostly covered by a securing cap 80, i.e. the securing cap reaches up to the socket elements 25, 27 in the closed state so that only a lower part of the closure element 50 which is directed toward the cartridge and contains the bayonet lugs 30, 32 and the coding nose 35 is exposed and is visible from the outside. The securing cap 80 has at its jacket surface a corrugation 85, which serves for the simpler handling of the securing cap 80. The corrugation 85 is made up of a number of webs extending parallel to the longitudinal axis of the securing cap 80, wherein the webs are arranged circumferentially over the whole periphery of the securing cap. The length of the webs is, however, shorter than the length of the jacket surface of the securing cap measured to the longitudinal axis of the securing cap, wherein the corrugation reaches up to the lower margin of the securing cap 80 directed toward the cartridge.

Figure 5:
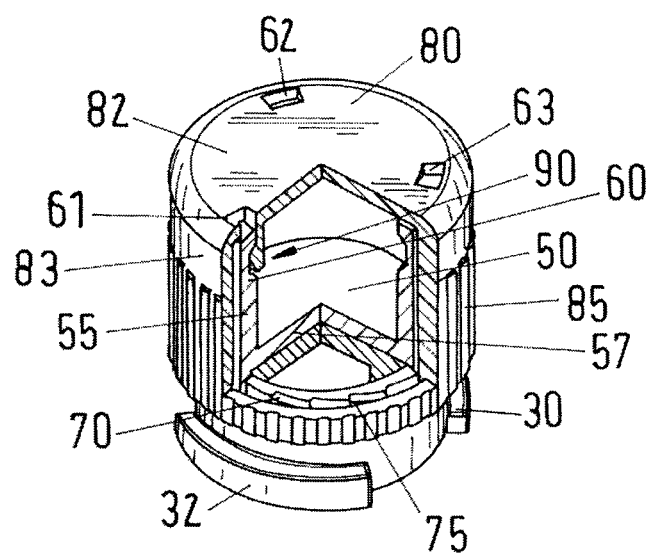
FIG. 5 is a perspective view of the closure shown in FIG. 4 in a partly open representation.

FIG. 5 shows a perspective view of the closure shown in FIG. 4 in a partly open representation. It can clearly be seen in FIG. 5 that the closure element 50 has a peripheral latch groove 60, into which spring elements 90 of the securing cap engage, at the inner side of the hollow cylindrical part 55 in the upper region, i.e. in the region facing away from the bayonet flanges. The securing cap 80 shown in FIG. 5 has three recesses 61, 62, 63 at its cover and a spring element 90 is molded to each of them. The latch groove 60 and the spring elements 90 together form a tongue and groove latch connection or a snap-in connection. The closure element 50 and the securing cap 80 form a unit due to the tongue and groove latch elements 60, 90, wherein the securing cap 80 is freely rotatable with respect to the closure element 50 in the mechanically non-stressed state, i.e. in the radially non-pressurized state, but the securing cap 80 is captively connected to the closure element 50, i.e. the closure is made up of a closure element 50 and of a securing cap 80 latched cohesively strongly thereto, but rotatably supported.

As can be seen from FIG. 5, the closure element 50 has at its jacket surface a saw tooth structure 70 which is made up of ribs in saw tooth form extending in the longitudinal direction of the closure element 50. The securing cap 80 has a saw tooth structure 75 corresponding thereto. As long as the securing cap 80 is not pressurized radially, the saw tooth structures 70, 75 of the closure element 50 and of the securing cap 80 do not engage into one another, i.e. the inner diameter of the securing cap 80, including the saw tooth structure, is larger than the outer diameter of the closure element including the saw tooth structure. The securing cap 80 is made from elastic material so that when a radial pressure a is exerted onto the securing cap 80, the saw tooth structures 70, 75 of the closure element 50 and of the securing cap 80 engage into one another and the closure element 50 can thereby be rotated in the direction b. The fixing to and also the removal of the closure 50, 80 from the cartridge 5 consequently requires a radial pressure movement a as well as a corresponding rotational movement b (see FIG. 4).

Figure 6:
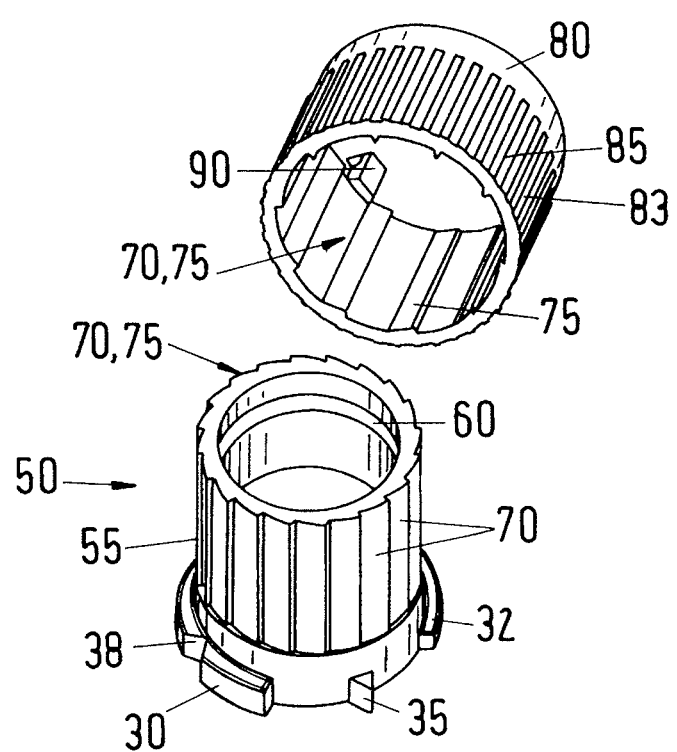
FIG. 6 is a perspective representation of the closure element and of the securing cap matching it of the closure shown in FIG. 5.

FIG. 6 shows a perspective representation of the closure element 50 and of the securing cap 80 matching it of the closure shown in FIG. 50. The closure element 50 shown in FIG. 6 has at the lower end of its cylindrical part 55 the segment-shaped bayonet lugs 30, 32, an outwardly open V-shaped notch 38 as a coding means and a coding nose 35 corresponding to a recess 23 (see FIG. 2, FIG. 4, FIG. 7) of the socket element 25 of the double cartridge. The jacket surface of the cylindrical part 55 of the closure element 50 shows a saw tooth structure 70, wherein this structure 70 is made up of ribs in saw tooth form extending in the longitudinal direction of the closure element 50. The peripheral latch groove 60 is located in the upper region at the inner side of the hollow cylindrical part 55 of the closure element 50.

FIG. 6 further shows a securing cap 80 matching the closure element 50 having a spring element 90 molded to the cover of the securing cap 80. The inner wall of the hollow cylindrical part 83 of the securing cap 80 has a saw tooth structure 75 corresponding to the saw tooth structure 70 of the closure element 50. The jacket surface of the securing cap 80 moreover has a corrugation 85 for better handling.

Figure 7:
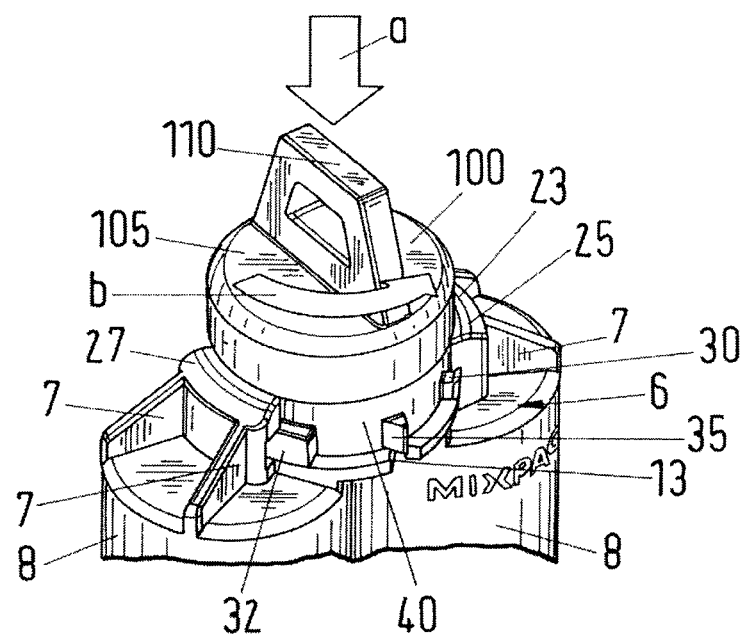
FIG. 7 is a perspective view of a second embodiment of a closure fastened onto a double cartridge by means of a bayonet closure.

FIG. 7 shows a perspective view of a second embodiment of a closure fastened onto a double cartridge by means of a bayonet closure. The double cartridge contains two containers 8 for the reception of at least one chemical component each. Segment-shaped socket elements 25, 27 are molded on the front side 6 of the cartridge and are stabilized in the radial direction by reinforcement ribs 7. The closure element 40 is of a cup-shaped or cap-shaped structure, wherein its exposed margin has a flange structure corresponding to the closure element 50 shown in FIGS. 4 to 6, i.e. the closure element 40 also has segment-shaped bayonet lugs 30, 32 and a coding nose 35 since the closure element 40 of a second kind should also fit onto a commercial double cartridge having a bayonet fastening means. Consequently, the closure element 40 can be fastened by means of bayonet lugs 30, 32 introduced into the segment-shaped groove 22 of the socket elements 25, 27 of the dispensing apparatus 5. The bayonet lugs 30, 32 and the coding noses 35 are preferably molded to the closure element 40 in one piece. The coding nose 35 in the shown closed state, i.e. with the bayonet lugs 30, 32 pushed into the socket elements of the cartridge, is aligned with the V-shaped notch 13 on the front side 6 of the cartridge. The closure element 40 is in turn very largely covered by a securing cap 100, i.e. the securing cap reaches up to the socket elements 25, 27 in the closed state so that only a lower part of the closure element 40 which is directed toward the cartridge and contains the bayonet lugs 30, 32 and the coding nose 35 is exposed and is visible from the outside. The securing cap 100 has at its cover element 105 a rotary hoop 110 which serves for the simpler handling of the securing cap 100.

Figure 8:
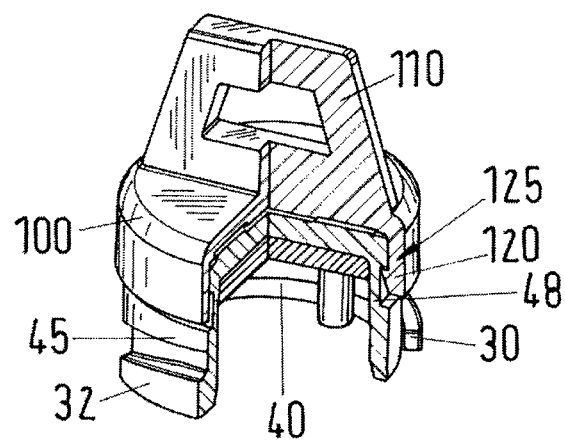
FIG. 8 is a perspective view of the closure shown in FIG. 7 in a partly open representation.

FIG. 8 shows a perspective view of the closure shown in FIG. 7 in a partly open representation. In FIG. 8, a peripheral groove which is called a latch groove 48 and serves for the engagement of spring elements 120 of the securing cap of a second kind is visible at the upper part of the jacket surface of the cylindrical part 45 of the closure element 40, i.e. at the side of the jacket surface of the closure element 40 facing away from the bayonet fastening means. The securing cap 100 shown in FIG. 8 has an exposed, peripheral margin which is configured either overall as a spring element 120 or has a number of separate spring elements 120, in particular three. The spring elements 120 are preferably configured as hook-shaped noses such that each of the hook-shaped noses can engage into the optionally slightly undercut latch groove 48. Since the securing cap and in particular its exposed margin is configured at least partly elastically, the securing cap 100 with the hook-shaped noses can be pushed over the closure element 40, wherein in the end position the hook-shaped noses engage behind the peripheral latch groove 48 so that the securing cap 100 is thereby captively fastened to the closure element 40. The latch groove 48 and the spring elements 120 configured as hook-shaped noses together form a tongue and groove latch connection 125 or a snap-in connection. The closure element 40 and the securing cap 100 form a unit due to the tongue and groove latch connection 125, wherein the securing cap 100 is freely rotatable with respect to the closure element 40 in the mechanically not stressed state, i.e. in state not pressurized axially in the direction of the longitudinal axis of the closure element 40 and of the securing cap 100, but the securing cap 100 is captively connected to the closure element 40, i.e. the closure is made up of a closure element 40 and of a securing cap 100 cohesively strongly latched thereto, but rotatably supported by the tongue and groove latch connection 125.

It can also be clearly seen from FIG. 8 that the rotary hoop 110 of the securing cap 100 as well as the spring elements 120 molded to the securing cap 100 form a unit with the securing cap, i.e. form a cast piece which preferably represents a plastic cast element.

Figure 9:
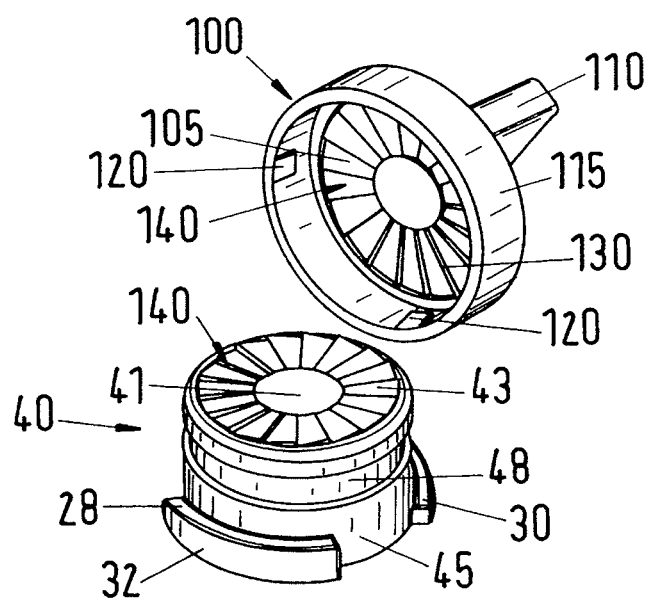
FIG. 9 is a perspective representation of the closure element and of the securing cap matching it of the closure shown in FIG. 8.

FIG. 9 shows a perspective representation of the closure element 40 and of the securing cap 100 matching it of the closure shown in FIG. 8.

The closure element 40 shown in FIG. 9 has the segment-shaped bayonet lugs 30 and 32 at the lower end of its cylindrical part 45. The upper surface of the bayonet lugs can in this respect have a chamfer 28 so that the initial introduction of the bayonet lugs 30, 32 into the socket elements 25 and 27 of the dispensing apparatus is facilitated.

The jacket surface of the cylindrical part 45 of the closure element 40 has, on the one hand, the peripheral latch groove 48 and the cover region has a radially extending saw tooth structure 43. The saw tooth structure 43 at the outer side of the cover of the closure element 40 is formed by radially extending ribs in saw tooth form, wherein the length of the ribs does not cover the whole radius of the cover region, but rather only approximately ½ to ⅔ of the outer region of the cover.

FIG. 9 further shows a securing cap 100 matching the closure element 40 and having spring elements 120 molded at the inner surface of the cylindrical part 115 of the closure element 100 in the region of the peripheral free end. The inner side of the cover part 105 of the securing cap 100 has a saw tooth structure 130 which corresponds to the saw tooth structure 43 of the closure element and is made up of radially extending ribs in saw tooth form. The closure cap 100 further has a rotational hoop 110 which serves for the simpler handling of the closure.

The closure element 40 and the securing cap 100 are configured such that the closure element 40 and the securing cap 100 are freely rotatable in their mutually latched state with a non-pressurized securing cap, i.e. the saw tooth structures 43 and 130 do not engage into one another, i.e. the spring elements 120 have a certain clearance in the latch groove 48. On the exertion of an axial pressure a, i.e. pressure in the direction of the dispensing apparatus of the double cartridge, onto the securing cap 100, the two saw tooth structures 43 and 130 engage into one another and thus form a saw tooth coupling 140. In the meshed state, the closure element 40 can also be rotated by rotating the securing cap 100 in direction b so that the closure made up of the closure element 40 and the securing cap 100 can be rotated in or out of the socket elements 30, 32 of the dispensing apparatus 5. The fixing to and also the removal of the closure from the cartridge 5 consequently requires an axial pressure movement a as well as a corresponding rotational movement b.

The invention claimed is:

1. A childproof closure for a dispensing apparatus comprising a dispensing apparatus having a first bayonet fastening means, a closure having a second bayonet fastening means, wherein one of the two bayonet fastening means has bayonet lugs which can be introduced into corresponding socket elements of the other bayonet fastening means, and both bayonet fastening means have coding elements for a preset alignment of the closure and of the dispensing apparatus, further wherein
the closure consists essentially of a closure element having first engagement elements and a securing cap at least partly covering the closure element and having engagement elements; the securing cap and the closure element are connected cohesively strongly, but rotatably with respect to one another by means of shape-matched elements; and the securing cap is configured at least partly elastically deformably such that the first and second engagement elements can be brought into engagement with one another by pressing the securing cap toward the closure element wherein the shape-matched elements of the closure element and of the securing cap are tongue and groove connection elements; and wherein the closure element is a beaker-like element having a hollow cylindrical part and a base and has a radially outwardly extending saw tooth structure at at least a part of the outer surface of its base; the securing cap is a beaker-like element having a hollow cylindrical part and a base, wherein the inner side of the base of the securing cap has a radially outwardly extending saw tooth structure which can engage into the saw tooth structure of the closure element.

2. A childproof closure in accordance with claim 1, wherein the securing cap represents a beaker-like element which is configured such that it can be pushed over the closure element.

3. A childproof closure in accordance with claim 1, wherein the securing cap is a beaker-like element which can be pushed over the closure element and which has a hollow cylindrical part and a base, wherein the securing cap has second engagement elements at its inner side.

4. A childproof closure in accordance with claim 1, wherein the securing cap is dimensioned such that the securing cap pushed over the closure element is freely rotatable in the mechanically non-stressed state with respect to the closure element.

5. A childproof closure in accordance with claim 1, wherein the engagement elements have a saw tooth structure.

6. A childproof closure in accordance with claim 1, wherein the closure element has a peripheral or sector-like latch groove extending transversely to its concentric longitudinal axis, and the securing cap has at least one spring element which can engage elastically into the latch groove of the closure element and is molded to the securing cap.

7. A childproof closure in accordance with claim 1, wherein the securing cap has a peripheral or sector-like grove extending transversely to its concentric longitudinal axis; and the closure element has at least one spring element which can engage elastically into the groove of the securing cap and which is molded to the closure element.

8. A childproof closure in accordance with claim 1, wherein the dispensing apparatus is a multicomponent cartridge, in particular a two-component cartridge.

9. A childproof closure in accordance with claim 1, wherein the socket elements represent ring-like or sector-like elements having an undercut for the at least partial shape-matched reception of the bayonet lugs.

10. A childproof closure in accordance with claim 9, wherein the coding elements are formed by cut-outs at the socket elements and bayonet lugs of different widths such that the bayonet lugs of the closure element or of the dispensing apparatus can be introduced in only one specific position with respect to the cut-outs of the ring-like or sector-like socket elements.

11. A childproof closure in accordance with claim 1, wherein the socket elements and the dispensing apparatus are configured in one piece in the form of a molded body, and the bayonet lugs are molded in one piece in the form of a molded body to the closure element.

12. A childproof closure in accordance with claim 1, wherein the socket elements and the closure element are configured in one piece in the form of a molded body, and the bayonet lugs are molded in one piece in the form of a molded body to the dispensing apparatus.

13. A childproof closure in accordance with claim 1, wherein the closure element has radially projecting segment-like bayonet lugs at the merging of its jacket surface directed toward the dispensing apparatus transversely to its concentric longitudinal axis.

14. A childproof closure in accordance with claim 1, wherein the securing cap is made completely of plastic.

* * * * *